US010012709B2

(12) United States Patent
Andronesi et al.

(10) Patent No.: US 10,012,709 B2
(45) Date of Patent: Jul. 3, 2018

(54) SYSTEM FOR OPTIMIZED LOW POWER MR IMAGING

(71) Applicants: Ovidiu Andronesi, Melrose, MA (US);
Bruce Rosen, Lexington, MA (US);
Peter Caravan, Cambridge, MA (US);
Himanshu Bhat, Cambridge, MA (US)

(72) Inventors: Ovidiu Andronesi, Melrose, MA (US);
Bruce Rosen, Lexington, MA (US);
Peter Caravan, Cambridge, MA (US);
Himanshu Bhat, Cambridge, MA (US)

(73) Assignees: The General Hospital Corporation, Boston, MA (US); Siemens Healthcare GmbH, Erlangen (DE)

( * ) Notice: Subject to any disclaimer, the term of this patent is extended or adjusted under 35 U.S.C. 154(b) by 1172 days.

(21) Appl. No.: 13/958,654

(22) Filed: Aug. 5, 2013

(65) Prior Publication Data
US 2014/0035580 A1    Feb. 6, 2014

Related U.S. Application Data

(60) Provisional application No. 61/679,856, filed on Aug. 6, 2012.

(51) Int. Cl.
*G01V 3/00* (2006.01)
*G01R 33/36* (2006.01)
(Continued)

(52) U.S. Cl.
CPC ......... *G01R 33/36* (2013.01); *G01R 33/5602* (2013.01); *A61B 5/055* (2013.01); *G01R 33/5616* (2013.01); *G01R 33/5617* (2013.01)

(58) Field of Classification Search
CPC ............... G01R 33/36; G01R 33/5602; G01R 33/5616; G01R 33/5617; A61B 5/055
(Continued)

(56) References Cited

U.S. PATENT DOCUMENTS 5,151,655 A * 9/1992 Harms ................. G01R 33/561
324/307
7,064,545 B2 * 6/2006 Zaharchuk ........... G01R 33/563
324/307
(Continued)

FOREIGN PATENT DOCUMENTS

WO    WO 2005043182 A1 *  5/2005  ......... G01R 33/4835
WO    WO 2006042120 A3 *  4/2006  ........... G01R 33/446

OTHER PUBLICATIONS

Dr. Lothar Schad, Physics of Imaging Systems Basic Principles of Magnetic Resonance Imaging V, Dec. 9, 2008, p. 22. http://www.umm.uni-heidelberg.de/inst/cbtm/ckm/lehre/techniquesofimagingsystems/12_medphys_mri_5_2sw.pdf.*
(Continued)

*Primary Examiner* — Susan Lee (57) ABSTRACT

A system acquires MR imaging data of a portion of patient anatomy associated with proton spin lattice relaxation time in a rotating frame using an RF (Radio Frequency) signal generator configured to generate RF excitation pulses and a magnetic field gradient generator configured to generate anatomical volume select magnetic field gradients for phase encoding and readout RF data acquisition. The RF signal generator and the gradient generator are configured to provide a rotating frame preparation pulse sequence comprising at least one of, (a) a T1 spin lattice relaxation in a rotating frame (T1ρ) preparation pulse sequence of adiabatic pulses comprising modulated RF pulses and modulated magnetic field gradients for slice selection and (b) a T2 spin-spin relaxation in a rotating frame (T2ρ) preparation pulse sequence of adiabatic pulses comprising modulated RF pulses and modulated magnetic field gradients for slice selection.

26 Claims, 8 Drawing Sheets

(51) Int. Cl.
  *G01R 33/56* (2006.01)
  *A61B 5/055* (2006.01)
  *G01R 33/561* (2006.01)
(58) Field of Classification Search
  USPC .......................................................... 324/309
  See application file for complete search history.

(56) References Cited

U.S. PATENT DOCUMENTS

| | | | | |
|---|---|---|---|---|
| 7,932,719 | B2* | 4/2011 | Liimatainen | G01R 33/50 324/307 |
| 8,076,936 | B2* | 12/2011 | Borthakur | A61B 5/055 324/309 |
| 8,374,411 | B2* | 2/2013 | Ernst | A61B 5/055 382/103 |
| 8,797,031 | B2* | 8/2014 | Rehwald | G01R 33/5602 324/309 |
| 2006/0244447 | A1* | 11/2006 | Michaeli | G01R 33/50 324/309 |
| 2009/0230958 | A1* | 9/2009 | Balchandani | G01R 33/4833 324/309 |
| 2010/0060277 | A1* | 3/2010 | Nezafat | G01R 33/5635 324/309 |
| 2010/0166278 | A1* | 7/2010 | Witschey | A61B 5/055 382/131 |
| 2012/0146639 | A1* | 6/2012 | Sorensen | G01R 33/4633 324/309 |
| 2012/0194187 | A1* | 8/2012 | Rehwald | G01R 33/5602 324/309 |

OTHER PUBLICATIONS

Wang et al., "Measuring T2 and T1, and Imaging T2 without Spin Echoes", Jan. 2012, J Magn Reson, 214(1): 273-280.*

Andronesi et al., "Low-power Adiabatic Sequences for In-vivo Localized Two-Dimensional Chemical Shift Correlated MR Spectroscopy", Dec. 2010, Magn Reson Med, 64(6): 1542-1556.*

Andronesi et al., Spectroscopic Imaging with Improved Gradient Modulated Constant Adiabaticity Pulses on High-Field Clinical Scanners, Jan. 2010, Journal of Magnetic Resonance, p. 283-293.*

Andronesi et al., Spectroscopic Imaging with Improved Gradient Modulated Constant Adiabaticity Pulses on High-Field Clinical Scanners, Jan. 2010, Journal of Magnetic Resonance, 203 (2010) pp. 283-293.*

Andronesi et al., Neurologic 3D MR Spectroscopic Imaging with Low-Power Adiabatic Pulses and Fast Spiral Acquisition, Feb. 2012, Radiology, 262, pp. 647-661.*

Andronesi et al., Low-Power Adiabatic Sequences for in Vivo Localized Two-Dimensional Chemical Shift Correlated MR Spectroscopy, Dec. 2010, Magnetic Resonance in Medicine, 64, pp. 1542-1556.*

Jokivarsi et al., Estimation of the Onset Time of Cerebral Ischemia Using T1p and T2 MRI in Rats, Jul. 2010, American Heart Association, pp. 2335-2340.*

Andrones et al., Combined Off-Resonance Imaging and T2 Relaxation in the Rotating Frame for Positive Contrast MR Imaging of Infection in a Murine Burn Model, Journal of Magnetic Resonance Imaging, Aug. 2010, 32, pp. 1172-1183.*

Haris, et al., "T1rho (T1p) MR imaging in Alzheimer' disease and Parkinson's disease with and without dementia", J Neurol (2011) 258:380-385.

Xiang YJ, et al., "T1p MR Imaging Is Sensitive to Evaluate Liver Fibrosis: An Experimental Study in a Rat Biliary Duct Ligation Model", Radiology: vol. 259: No. 3, Jun. 2011.

Borthakur, et al., "T1P Magnetic Resonance Imaging and Discography Pressure as Novel Biomarkers for Disc Degeneration and Low Back Pain", Spine, vol. 36, No. 25, pp. 2190-2196, 2011.

Ovidiu C Andronesi, et al., "Low-Power Adiabatic Sequences for in Vivo Localized Two-Dimensional Chemical Shift Correlated MR Spectroscopy", Magnetic Resonance in Medicine 64: 1542-1556 (2010).

* cited by examiner

SYSTEM FOR OPTIMIZED LOW POWER MR IMAGING

CROSS-REFERENCE TO RELATED APPLICATIONS

This application claims priority to U.S. provisional application Ser. No. 61/679,856 filed Aug. 6, 2012, which is incorporated herein by reference in its entirety.

TECHNOLOGY FIELD

This invention relates to a system for acquiring MR imaging data of a portion of patient anatomy associated with proton spin-lattice and spin-spin relaxation times in the rotating frame.

BACKGROUND

MR imaging is a medical imaging technique that uses an applied magnetic field and RF pulses to make images of organs and structures inside the body. During MR imaging, the magnetic field causes magnetic field vectors of protons (typically in hydrogen atoms) to align with the magnetic field. The RF pulses cause the magnetic field vectors of the protons to be displaced from the magnetic field and re-align with the magnetic field. An MRI scanner picks up signals from the protons in the body that result from the magnetic field vectors re-aligning with the magnetic field. The signals may then be converted into images based on the location and strength of the incoming signals.

The rotating frame is the coordinate system that rotates about Z axis at the Larmor frequency of the scanner. In the rotating frame, a magnetization vector rotating at the Larmor frequency in the laboratory frame appears stationary. T1rho (or "T-1-rho") is the spin lattice relaxation time constant in the rotating frame, which determines the recovery of the longitudinal magnetization (along the effective field) in the presence of a "spin-lock" radio-frequency field and is an alternate MRI contrast method to visualize early pathological changes. T2rho (or "T-2-rho") is the spin-spin relaxation time constant in the rotating frame, which determines the decay of the transverse magnetization (perpendicular to the effective field) in the presence of a "spin-lock" radio-frequency field and is an alternate MRI contrast method to visualize early pathological changes.

SUMMARY

Embodiments of the present invention are directed to a system for acquiring MR imaging data of a portion of patient anatomy associated with proton spin lattice relaxation time in a rotating frame. The system includes an RF (Radio Frequency) signal generator configured to generate RF excitation pulses in an anatomy and enabling subsequent acquisition of associated RF echo data. The system also includes a magnetic field gradient generator configured to generate anatomical volume select magnetic field gradients for phase encoding and readout RF data acquisition in a three dimensional (3D) anatomical volume. The RF signal generator and the gradient generator provide a rotating frame preparation pulse sequence comprising at least one of: (a) a T1 spin lattice relaxation in a rotating frame (T1ρ) preparation pulse sequence of adiabatic pulses comprising modulated RF pulses and modulated magnetic field gradients for slice selection; and (b) a T2 spin-spin relaxation in a rotating frame (T2ρ) preparation pulse sequence of adiabatic pulses comprising modulated RF pulses and modulated magnetic field gradients for slice selection.

According to one embodiment of the invention, the RF signal generator and said gradient generator use a readout gradient for RF data acquisition. The rotating frame preparation pulse sequence of adiabatic pulses and readout RF data acquisition enable acquisition of a plurality of image slices within a single imaging scan.

According to another embodiment of the invention, the single imaging scan includes a programmed acquisition of MR image data without user interaction in controlling an MRI scanner.

In one embodiment, the rotating frame preparation pulse sequence of adiabatic pulses and readout RF data acquisition enable acquisition of said plurality of image slices that include at least one of: (a) 20 slices with (echo planar imaging) EPI based data acquisition; and (b) 128 slices with 3D TFL (turbo-FLASH) based data acquisition.

In an aspect of an embodiment, the rotating frame preparation pulse sequence of adiabatic pulses and readout RF data acquisition enable acquisition of said plurality of image slices that include at least one of: (a) 20 slices with EPI based data acquisition within 1.5 minutes; and (b) 128 slices with 3D TFL (turbo-FLASH) based data acquisition within 7.21 minutes.

According to one embodiment of the invention, the rotating frame preparation pulse sequence of adiabatic pulses and readout RF data acquisition enable acquisition of said plurality of image slices with a reduced Specific Absorption Rate enabling accelerated image acquisition of said plurality of image slices within a single scan.

According to another embodiment of the invention, the T1ρ spin lattice relaxation is obtained when proton spin magnetization is locked along the direction of an effective magnetic field in response to RF pulse amplitude and RF offset modulation.

In one embodiment, the T2ρ spin-spin relaxation is obtained in response to proton spin magnetization being perpendicular and precessing around the direction of an effective magnetic field resulting from an RF pulse amplitude and RF offset modulation.

In another embodiment, the modulated RF pulses and modulated magnetic field gradients for slice selection comprise a Gradient Offset Independent Adiabaticity pulse with Wurst modulation (GOIA-W) for both RF and gradient.

In an aspect of an embodiment, a modulation function is $$RF(t) = RF_{max}\left(1 - \left|\sin\left(\frac{\pi}{2}\left(\frac{2t}{T_p} - 1\right)\right)\right|^n\right)$$

$$G(t) = G_{max}\left((1-f) + f\left|\sin\left(\frac{\pi}{2}\left(\frac{2t}{T_p} - 1\right)\right)\right|^m\right)$$

where Tp is the pulse duration (0<t<Tp), RFmax is a maximum RF amplitude, where Tp is the pulse duration (0<t<Tp), RFmax is a maximum RF amplitude, Gmax is a maximum gradient, f [0, 1] is the gradient modulation factor, GOIA-W pulses comprises GOIA-W(n, m), where n and m are the orders for the RF and gradient modulation functions respectively and are chosen to be different (m<n) and the functions comprise at least one of GOIA-W(16,4) and GOIA-W(16,3).

According to one embodiment, the readout RF data acquisition includes at least one of: a spin echo or gradient echo EPI (Echoplanar imaging); TFL (Turbo-FLASH); or TSE (Turbo-spin echo) pulse sequence acquisition.

According to another embodiment, the rotating frame preparation pulse sequence of adiabatic pulses acquires a plurality of different images at a corresponding plurality of T1ρ or T2ρ preparation times having a range of 0-100 msec. The system further includes an image data processor configured to generating a composite T1ρ or T2ρ image map from said plurality of different images.

In an aspect of an embodiment, the rotating frame preparation pulse sequence of adiabatic pulses enables generation of said composite T1ρ or T2ρ image map from said plurality of different images within at least one of, (a) 1.5 minutes with EPI data acquisition and (b) 7.21 minutes with TFL (Turbo-FLASH) based data acquisition.

Embodiments of the present invention are directed to a method for acquiring MR imaging data of a portion of patient anatomy associated with proton spin lattice relaxation time in a rotating frame. The method includes generating, via an RF (Radio Frequency) signal generator, RF excitation pulses in an anatomy. The method also includes enabling, via said RF (Radio Frequency) signal generator, subsequent acquisition of associated RF echo data and generating, via a magnetic field gradient generator, anatomical volume select magnetic field gradients for phase encoding and readout RF data acquisition in a three dimensional (3D) anatomical volume. The RF signal generator and the gradient generator providing a rotating frame preparation pulse sequence comprising at least one of: a T1 spin lattice relaxation in a rotating frame (T1ρ) preparation pulse sequence of adiabatic pulses comprising modulated RF pulses and modulated magnetic field gradients for slice selection; and a T2 spin-spin relaxation in a rotating frame (T2ρ) preparation pulse sequence of adiabatic pulses comprising modulated RF pulses and modulated magnetic field gradients for slice selection.

According to one embodiment, the method further includes using a readout gradient for RF data acquisition. The rotating frame preparation pulse sequence of adiabatic pulses and readout RF data acquisition enable acquisition of a plurality of image slices within a single imaging scan.

According to another embodiment, the single imaging scan includes a programmed acquisition of MR image data without user interaction in controlling an MRI scanner.

According to an aspect of an embodiment, the single rotating frame preparation pulse sequence of adiabatic pulses and readout RF data acquisition enable acquisition of said plurality of image slices comprising at least one of: (a) 20 slices with (echo planar imaging) EPI based data acquisition; and (b) 128 slices with 3D TFL (turbo-FLASH) based data acquisition.

According to another aspect of an embodiment, the rotating frame preparation pulse sequence of adiabatic pulses and readout RF data acquisition enable acquisition of said plurality of image slices comprising at least one of: (a) 20 slices with EPI based data acquisition within 1.5 minutes; and (b) 128 slices with 3D TFL (turbo-FLASH) based data acquisition within 7.21 minutes.

In one embodiment, the said rotating frame preparation pulse sequence of adiabatic pulses and readout RF data acquisition enable acquisition of said plurality of image slices with reduced Specific Absorption Rate enabling accelerated image acquisition of said plurality of image slices within a single scan.

In another embodiment, the T1ρ spin lattice relaxation is obtained when proton spin magnetization is locked along the direction of a magnetic field in response to RF pulse amplitude and RF offset modulation.

In one aspect of an embodiment, the T2ρ spin-spin relaxation is obtained in response to proton spin magnetization being perpendicular and precessing around the direction of a magnetic field resulting from an RF pulse amplitude and RF offset modulation.

In another aspect of an embodiment, the modulated RF pulses and modulated magnetic field gradients for slice selection include a Gradient Offset Independent Adiabaticity pulse with Wurst modulation (GOIA-W) for both RF and gradient.

According to one embodiment, the readout RF data acquisition includes at least one of: a spin echo or gradient echo EPI (Echoplanar imaging); TFL (Turbo-FLASH) or TSE (Turbo-spin echo) pulse sequence acquisition.

According to one embodiment, the rotating frame preparation pulse sequence of adiabatic pulses acquires a plurality of different images at a corresponding plurality of T1ρ or T2ρ preparation times having a range of 0-100 msec. The method further includes generating, via an image data processor, a composite T1ρ or T2ρ image map from said plurality of different images.

Embodiments of the present invention are directed to a non-transitory, tangible computer-readable medium having instructions stored thereon for causing a processor to execute a method for acquiring MR imaging data of a portion of patient anatomy associated with proton spin lattice relaxation time in a rotating frame. The method includes generating RF excitation pulses in an anatomy and enabling subsequent acquisition of associated RF echo data. The method also includes generating anatomical volume select magnetic field gradients for phase encoding and readout RF data acquisition in a three dimensional (3D) anatomical volume. The method further includes providing a rotating frame preparation pulse sequence comprising at least one of: (a) a T1 spin lattice relaxation in a rotating frame (T1ρ) preparation pulse sequence of adiabatic pulses comprising modulated RF pulses and modulated magnetic field gradients for slice selection; and (b) a T2 spin-spin relaxation in a rotating frame (T2ρ) preparation pulse sequence of adiabatic pulses comprising modulated RF pulses and modulated magnetic field gradients for slice selection.

DETAILED DESCRIPTION EXEMPLARY EMBODIMENTS OF THE INVENTION

T1 and T2 relaxation in a rotating frame (T1rho and T2rho respectively) are sensitive to slow molecular dynamics on a millisecond time scale which is relevant for many important biological reactions, such as receptor binding, water exchange and binding of contrast agents to proteins. In conventional studies, T1rho has been related to protein content, and has been exploited to investigate pathology of stroke, Alzheimer's disease, liver cirrhosis, and cartilage damage. Because T1rho luminance contrast is created by the application of a long spin lock RF field or by a train of adiabatic inversion pulses, the resulting MRI pulse sequence has high specific absorption rate (SAR) and it is not spatially selective. As a result, a long TR time is typically needed, leading to long scanning times, low spatial resolution, reduced brain coverage and often due to these limitations the measurements comprise one to four slices. Further, conventional rotating frame (T1rho and T2rho) imaging methods are limited by high specific absorption rate (SAR), long acquisition times, reduced spatial coverage, sensitivity to B1 inhomogeneity and offsets of a main B0 field.

Embodiments of the present invention provide a system that acquires MR imaging data of a portion of patient anatomy associated with proton spin lattice relaxation time in a rotating frame. An RF (Radio Frequency) signal generator generates RF excitation pulses in anatomy and enables subsequent acquisition of associated RF echo data. A magnetic field gradient generator generates anatomical volume select magnetic field gradients for phase encoding and readout RF data acquisition in a three dimensional (3D) anatomical volume. The RF signal generator and the gradient generator provide a rotating frame preparation pulse sequence comprising at least one of: (a) a T1 spin lattice relaxation in a rotating frame (T1ρ) preparation pulse sequence of adiabatic pulses comprising modulated RF pulses and modulated magnetic field gradients for slice selection; and (b) a T2 spin-spin relaxation in a rotating frame (T2ρ) preparation pulse sequence of adiabatic pulses comprising modulated RF pulses and modulated magnetic field gradients for slice selection.

Embodiments provide a system that includes low power adiabatic MRI T1rho imaging with increased spatial coverage and short acquisition time. The system uses a pulse sequence comprising a T1rho pulse sequence based on low power gradient offset independent adiabatic pulses (Gradient Offset Independent Adiabacity with Wurst 16 and 4 modulation GOIA-W(16,4) pulses). The pulse sequence decreases the SAR and provides shorter repetition time TR (time between successive RF excitation pulses) and multislice acquisition in a feasible amount of time.

Figure 1:
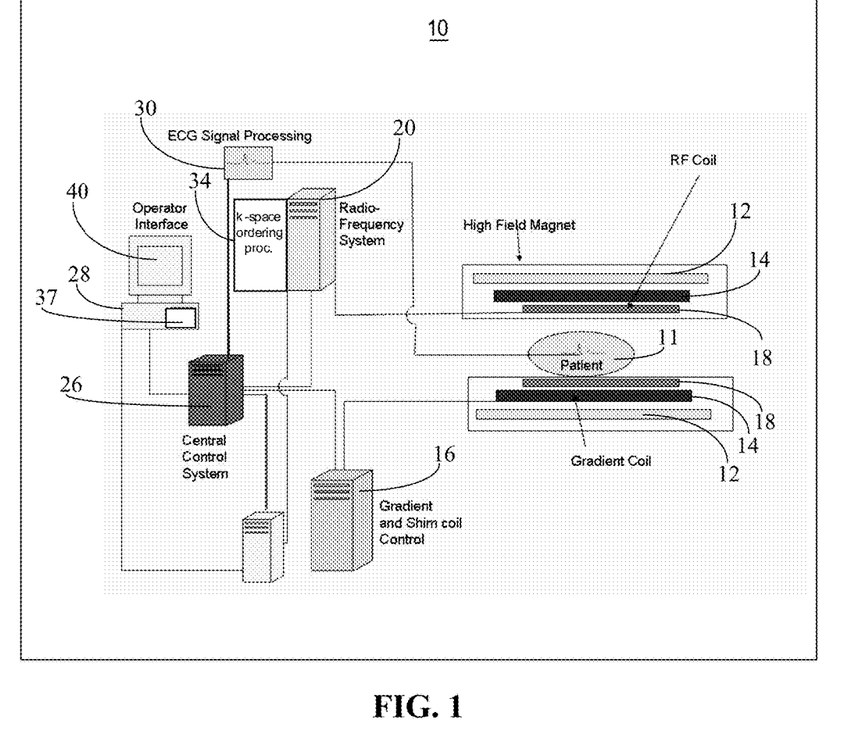
FIG. 1 is a block diagram illustrating an exemplary system for acquiring MR imaging data of a portion of patient anatomy associated with proton spin lattice relaxation time in a rotating frame according to embodiments disclosed herein.

FIG. 1 is a system block diagram illustrating a system 10 for acquiring MR imaging data of a portion of patient anatomy associated with proton spin lattice relaxation time in a rotating frame. As shown at FIG. 1, magnet 12 creates a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shimming and pulse sequence control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further, RF (radio frequency) module 20 provides RF pulse signals to RF coils 18, which in response produce magnetic field pulses which rotate the spins of the protons in the imaged body 11 by ninety degrees or by one hundred and eighty degrees for so-called "spin echo" imaging, or by angles less than or equal to 90 degrees for so-called "gradient echo" imaging. Pulse sequence control module 16, in conjunction with RF module 20 as directed by central control unit 26, control slice-selection, phase-encoding, readout gradient magnetic fields, radio frequency transmission, and magnetic resonance signal detection to acquire magnetic resonance signals representing planar slices of patient 11.

In response to applied RF pulse signals, the RF coils 18 receive MR signals, For example, RF coils 18 may receive signals from the excited protons within the body as they return to an equilibrium position established by the static and gradient magnetic fields. The MR signals are detected and processed by a detector within RF module 20 and k-space component processor unit 34 to provide image representative data to an image data processor in central control unit 26. ECG synchronization signal generator 30 provides ECG signals used for pulse sequence and imaging synchronization. A two or three dimensional k-space storage array of individual data elements in unit 34 stores corresponding individual frequency components comprising an MR dataset.

An RF (Radio Frequency) signal generator comprising module 20 and RF coils 18 generates RF excitation pulses in anatomy of patient 11 and enables subsequent acquisition of associated RF echo data. A magnetic field gradient generator (comprising magnetic coils 12 and 14) generates a magnetic field for use in acquiring multiple individual frequency components and generates magnetic field gradients for anatomical slice selection, phase encoding and readout RF data acquisition in a three dimensional (3D) anatomical volume. The RF signal generator units 18 and 20 and the magnetic field gradient generator units 12 and 14 provide a rotating frame preparation pulse sequence comprising at least one of:

(a) a T1 spin lattice relaxation in a rotating frame (T1ρ) preparation pulse sequence of adiabatic pulses comprising modulated RF pulses and modulated magnetic field gradients for slice selection; and (b) a T2 spin-spin relaxation in a rotating frame (T2ρ) preparation pulse sequence of adiabatic pulses comprising modulated RF pulses and modulated magnetic field gradients for slice selection.

Figure 4A:
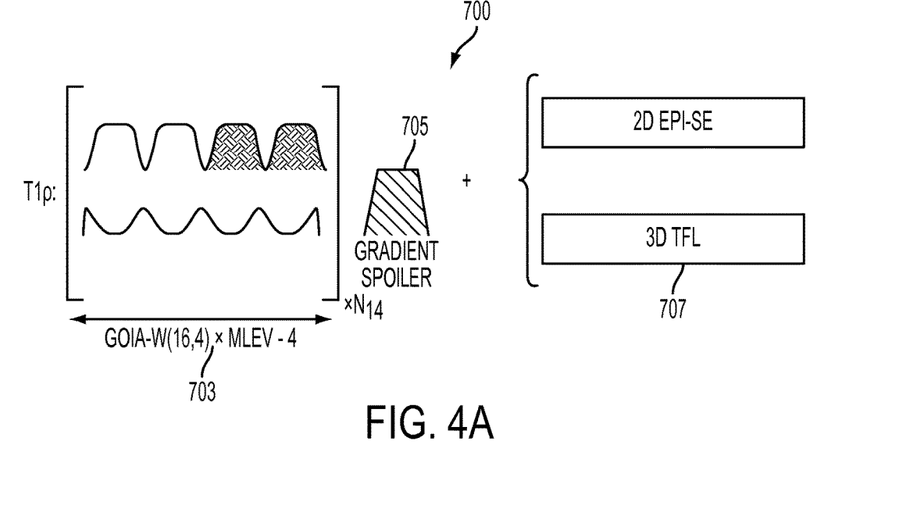
FIG. 4A is an illustration showing an exemplary T1 spin lattice relaxation in a rotating frame (T1ρ) preparation pulse sequence of adiabatic pulses according to embodiments disclosed herein.

FIG. 4A is an illustration showing a T1 spin lattice relaxation in a rotating frame (T1ρ) preparation pulse sequence of adiabatic pulses 700. T1rho rotating frame preparation pulse sequence 700 employs adiabatic pulses comprising modulated RF pulses and modulated magnetic field gradients for slice selection 703 of N repetitions (TR), followed by spoiler gradient pulse 705 and 2D EPI-SE (echo planar imaging spin echo) or 3D Turbo-FLASH (TFL) readout 707.

Figure 4B:
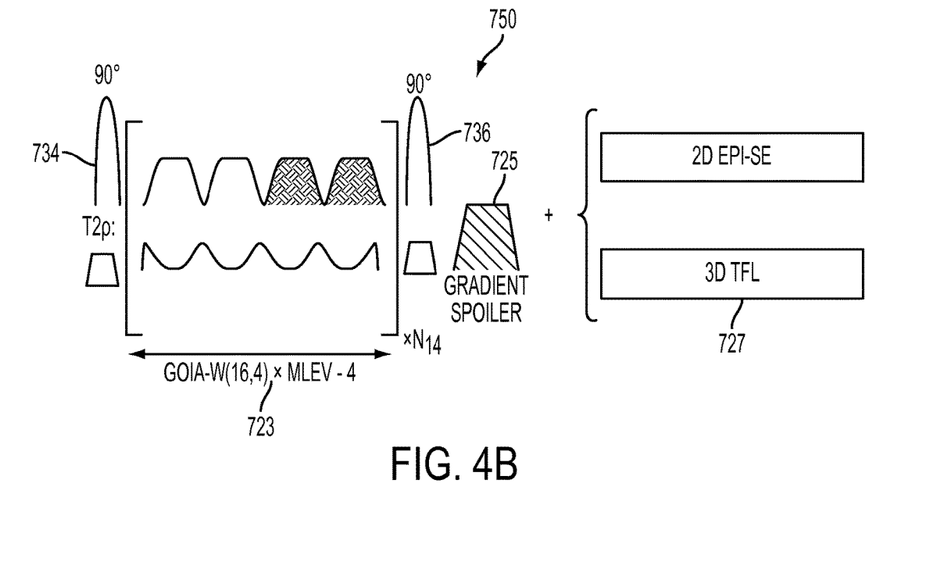
FIG. 4B is an illustration showing an exemplary T2 spin-spin relaxation in a rotating frame (T2ρ) preparation pulse sequence of adiabatic pulses according to embodiments disclosed herein.

FIG. 4B is an illustration showing a T2 spin-spin relaxation in a rotating frame (T2ρ) preparation pulse sequence of adiabatic pulses 750. T1rho rotating frame preparation pulse sequence 750 employs adiabatic pulses comprising modulated RF pulses and modulated magnetic field gradients for slice selection 723 of N repetitions (TR), preceded by a 90 degree RF pulse 734 and followed by a 90 degree RF pulse 736, spoiler gradient pulse 725 and 2D EPI-SE (echo planar imaging spin echo) or 3D Turbo-FLASH (TFL) readout 727.

Figure 5:
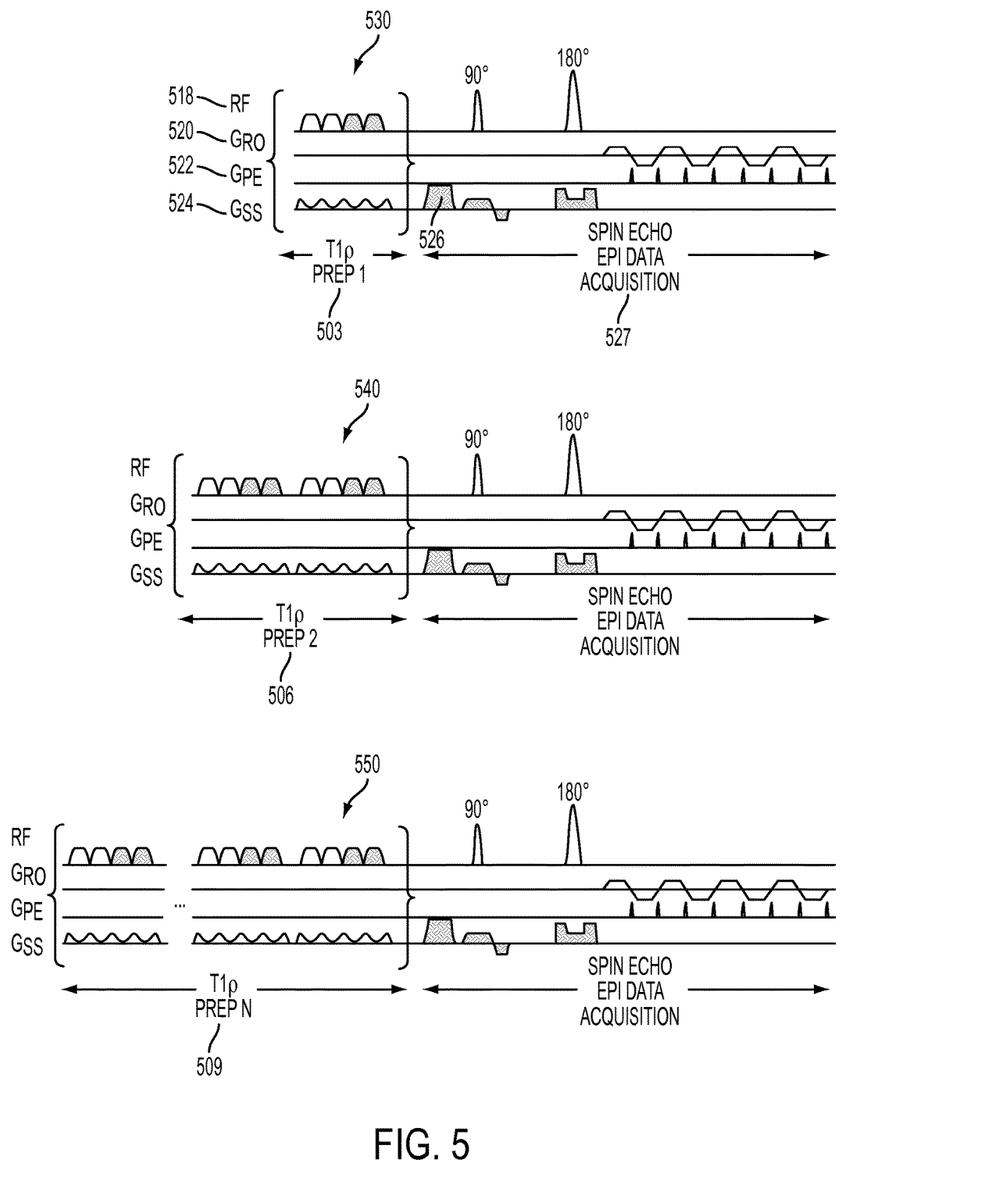
FIG. 5 is an illustration showing an exemplary T1 spin lattice relaxation in a rotating frame (T1ρ) preparation pulse sequence of adiabatic pulses comprising modulated RF pulses and modulated magnetic field gradients for slice selection according to embodiments disclosed herein.

FIG. 5 is an illustration showing a T1 spin lattice relaxation in a rotating frame (T1ρ) preparation pulse sequences 530, 540 and 550 of adiabatic pulses comprising modulated RF pulses and modulated magnetic field gradients for slice selection. Pulse sequence 530 shows adiabatic pulses for a single excitation period 503 comprising modulated RF pulses 518, readout magnetic field gradient GRO 520, phase encoding magnetic field gradient GPE 522 and modulated magnetic field gradients for slice selection GSS 524. The adiabatic pulses for single excitation period 503 are followed by spoiler gradient pulse 526. Subsequent pulse sequence 527 comprises a spin echo EPI readout and data acquisition pulse sequence. Similarly, pulse sequence 540 shows adiabatic pulses for two excitation periods 506 and pulse sequence 550 shows adiabatic pulses for N excitation periods 509.

Figure 6:
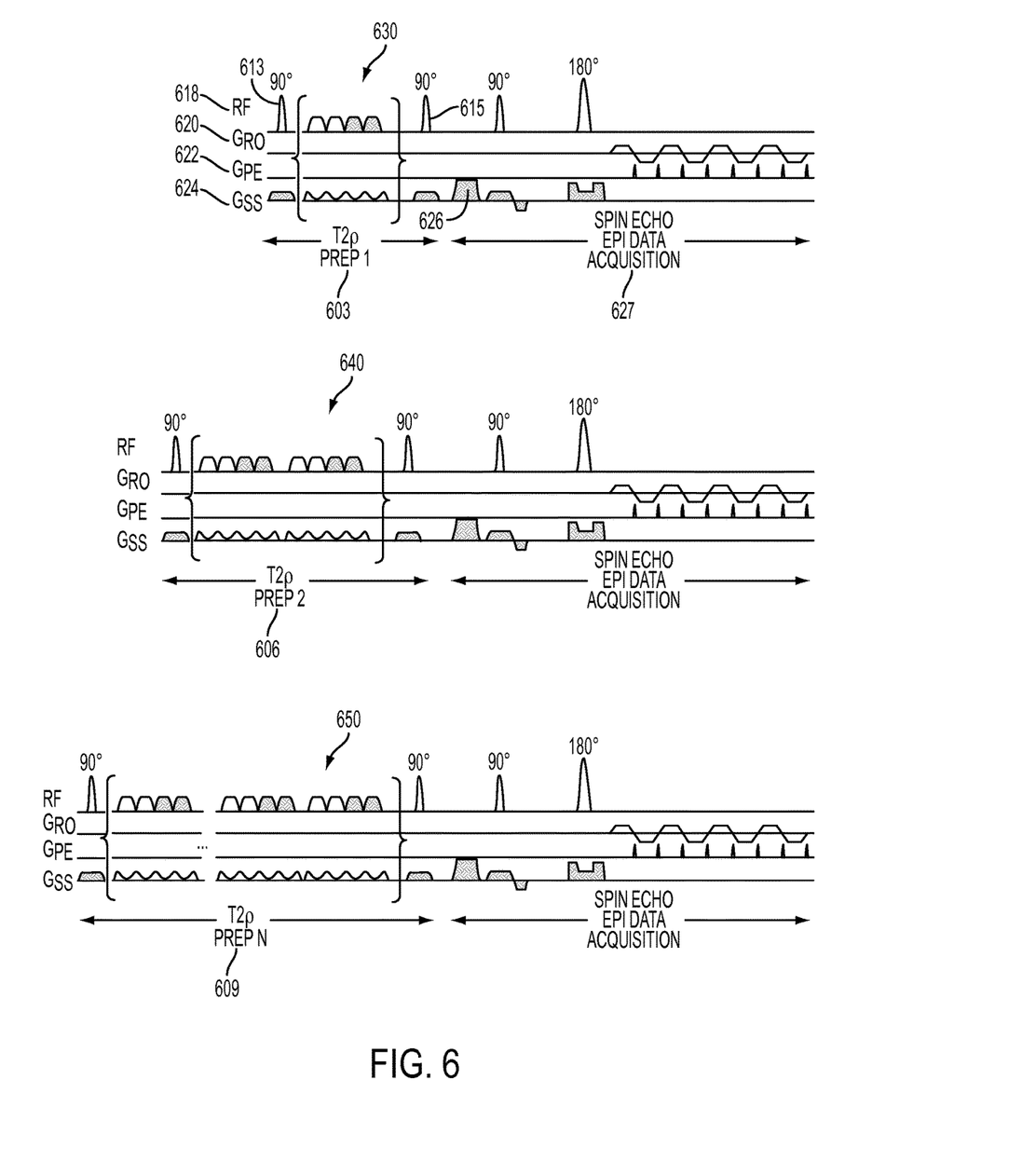
FIG. 6 is an illustration showing an exemplary T2 spin-spin relaxation in a rotating frame (T2ρ) preparation pulse sequence of adiabatic pulses comprising modulated RF pulses and modulated magnetic field gradients for slice selection according to embodiments disclosed herein.

FIG. 6 is an illustration showing a T2 spin-spin relaxation in a rotating frame (T2ρ) preparation pulse sequences 630, 640 and 650 of adiabatic pulses comprising modulated RF pulses and modulated magnetic field gradients for slice selection. Pulse sequence 630 shows adiabatic pulses for a single excitation period 603 comprising modulated RF pulses 618, readout magnetic field gradient GRO 620, phase encoding magnetic field gradient GPE 622 and modulated magnetic field gradients for slice selection GSS 624. The adiabatic pulses for single excitation period 603 are preceded by a 90 degree RF pulse 613 and followed by a 90 degree RF pulse 615 and spoiler gradient pulse 626. Subsequent pulse sequence 627 comprises a spin echo EPI readout and data acquisition pulse sequence. Similarly, pulse sequence 640 shows adiabatic pulses for two excitation periods 606 and pulse sequence 650 shows adiabatic pulses for N excitation periods 609.

Returning to FIG. 1, central control unit 26 uses information stored in an internal database to process the detected MR signals in a coordinated manner to generate high quality images of a selected slice (or slices) of the body and adjusts other parameters of system 10. The stored information comprises predetermined pulse sequence and magnetic field gradient and strength data as well as data indicating timing, orientation and spatial volume of gradient magnetic fields to be applied in imaging. Generated images are presented on display 40. Computer 28 includes a graphical user interface (GUI) enabling user interaction with central controller 26 and enables user modification of magnetic resonance imaging signals in substantially real time. Display processor 37 processes the magnetic resonance signals to provide image representative data for display on display 40, for example.

Figure 2:
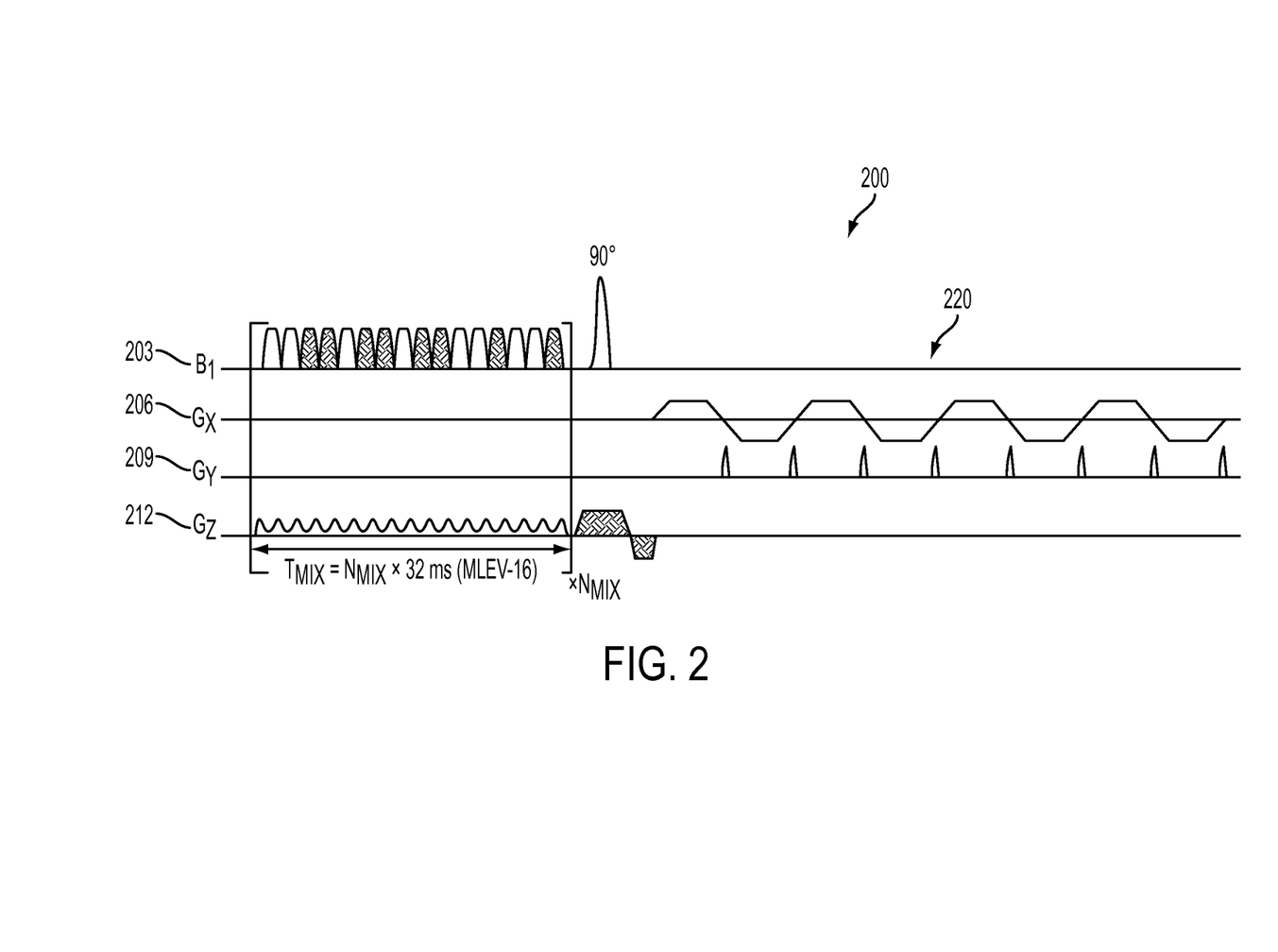
FIG. 2 is an illustration showing an exemplary low power adiabatic T1rho sequence with GOIA-W(16,4) pulses and EPI readout according to embodiments disclosed herein.

FIG. 2 is an illustration showing exemplary low power adiabatic T1rho rotating frame preparation pulse sequence 200 with GOIA-W (16,4) pulses and Echo planar imaging (EPI) readout sequence 220. In an exemplary embodiment, pulse sequence 200 is used on a whole-body 3 Tesla (e.g., Tim Trio clinical scanner Siemens, Erlangen, Germany). A body coil is used for RF transmission and a 32-channel head coil for RF reception. A GOIA-W (16,4) adiabatic pulses of 2.5 ms duration, 10 kHz bandwidth, 1 kHz maximum amplitude is used to construct a T1rho module according to MLEV-16 or MLEV-4 schemes. A single shot 2D EPI readout is used. Typical acquisition parameters of T1rho images are: TR=1s (per slice), TE=18 ms, FOV=240×240 mm$^2$, 96×96 matrix, in plan resolution of 2.5×2.5 mm$^2$, 10 slices, 5 mm slice thickness, 10 increments of the spin lock time, total acquisition time of 1:30 min:sec. The T1rho maps are obtained by fitting an equation for longitudinal relaxation in the rotating frame $I(t_{s1})=I(0)*exp(-t_{s1}/T1rho)$. Details of the pulse sequence diagram are provided in FIG. 2.

T1rho rotating frame preparation pulse sequence 200 employs adiabatic pulses comprising modulated RF pulses 203 and orthogonal coordinate magnetic field gradient pulse sequences Gx 206, Gy 209 with modulated magnetic field gradients Gz 212, for slice selection. Pulse sequence 200 in one embodiment comprises a GOIA-W(16,4) sequence (Gradient Offset Independent Adiabacity with Wurst 16 and 4 modulation). The RF sequence 203 uses WURST-16, and gradient Gz 212 uses WURST-4. In another embodiment sequence 200 uses GOIA-HS(8,4) based on hyperbolic sechant modulations. System 10 advantageously uses GOIA-W(16,4) pulses to generate T1rho and T2rho contrast and is slice selective, hence a shorter repetition time is used without saturating spins of an entire subject, requires low power deposition to achieve adiabatic rotating frame spin lock and enables reduction in image data acquisition time due to being slice selective and having relatively low SAR.

Figure 3A:
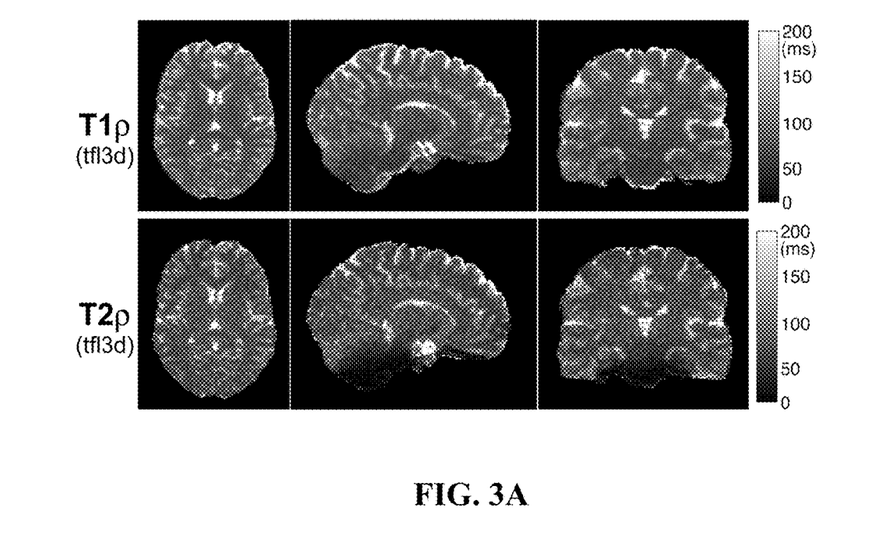
FIG. 3A is an illustration showing exemplary brain T1rho and T2 rho maps calculated using the 3d turbo flash readout in a 3 Tesla (T) MRI scanner according to embodiments disclosed herein.
Figure 3B:
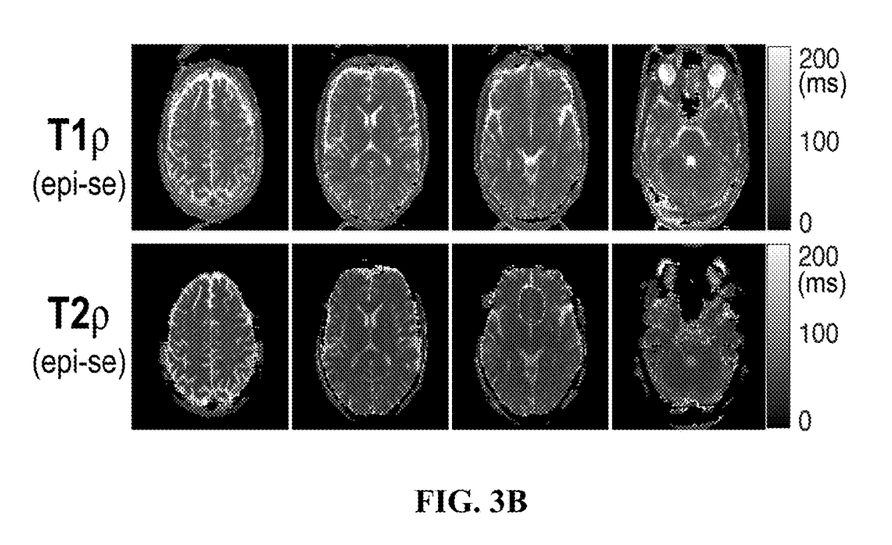
FIG. 3B is an illustration showing exemplary T1rho and T2rho maps calculated using the 2d multi-slice spin echo EPI readout in a 3 Tesla (T) MRI scanner according to embodiments disclosed herein.

FIG. 3A is an illustration showing exemplary brain T1rho and T2rho maps calculated by fitting the corresponding weighted images acquired in a healthy patient using a 3 Tesla (3T) MRI scanner. Images in FIG. 3A were acquired with a 3D turbo FLASH readout as described in FIGS. 4-6. FIG. 3B shows T1rho and T2rho maps calculated by fitting the corresponding weighted images acquired in a healthy patient using a 3 Tesla (3T) MRI scanner. Images in FIG. 3B were acquired with a 2D multi-slice spin echo EPI readout as described in FIGS. 4-6. The system advantageously employs a low power adiabatic T1rho sequence usable at 3T, for example, for human imaging, enabling multislice acquisition in a feasible amount of time. The pulse sequence is useful for investigating pathology in the brain and other organs.

In some embodiments, system 10 may advantageously provide T1rho weighted MRI sequences that are sensitive to a molecular environment. Known preparation methods for T1rho luminance contrast MR imaging are spatially non selective requiring delay until luminance contrast disappears from the slices before subsequent RF excitation may be performed, introducing an additional time limitation. In some conventional methods, T1rho luminance contrast may be transformed to be slice selective. These methods may, however, be limited by high specific absorption rate (SAR), long acquisition times, reduced spatial coverage, sensitivity to B1 inhomogeneity and offsets of B0 field.

In some embodiments, system 10 may advantageously use gradient modulated adiabatic pulses (for example, GOIA-W(16,4) pulses) that have reduced power requirements enabling shorter acquisition time and increased spatial coverage and resolution in feasible amounts of time for clinical use. Accordingly, system 10 may advantageously perform slice selective preparation for molecular luminance contrast MR imaging reducing repetition time TR because preparation to recover for the slices imaged may no longer be needed.

Conventional preparation methods for T1rho contrast are spatially non selective and require waiting for luminance contrast to disappear for slices before repeat RF excitation, introducing an additional time limitation. In one embodiment, system 10 advantageously uses slice profiles of GOIA-W(16,4) pulses which are sharp, have a wide bandwidth, and low power. Wide bandwidth GOIA-W(16,4) pulses reduce effect of offsets in B0 field for this type of contrast. Conventional systems fail to achieve such a wide bandwidth as provided by GOIA-W(16,4) within acceptable SAR limits.

According to an embodiment, system 10 performs T1rho spin lock MR imaging using wide bandwith low power gradient modulated adiabatic pulses in a slice selective manner. Readout may use EPI (Echoplanar imaging), TFL (Turbo-FLASH) or TSE (Turbo-spin echo). The slice selection is achieved by a gradient that is used during GOIA pulses. The gradient modulation enables reduction of B1 max due to VERSING of the pulse and is slice selective. In different embodiments, GOIA-HS(8,4) or GOIA-W(16,4) pulses may be used, for example. The system 10 pulse sequence may advantageously provide a short TR and in addition slice selection so the acquisition time is accelerated for fast acquisition of a T1rho map with EPI readout and compensating for B0 and B1 inhomegeneity artifacts in T1rho. In another embodiment, conventional adiabatic pulses are used together with gradients for slice selection, but may have higher SAR and may need longer TR.

Figure 7:
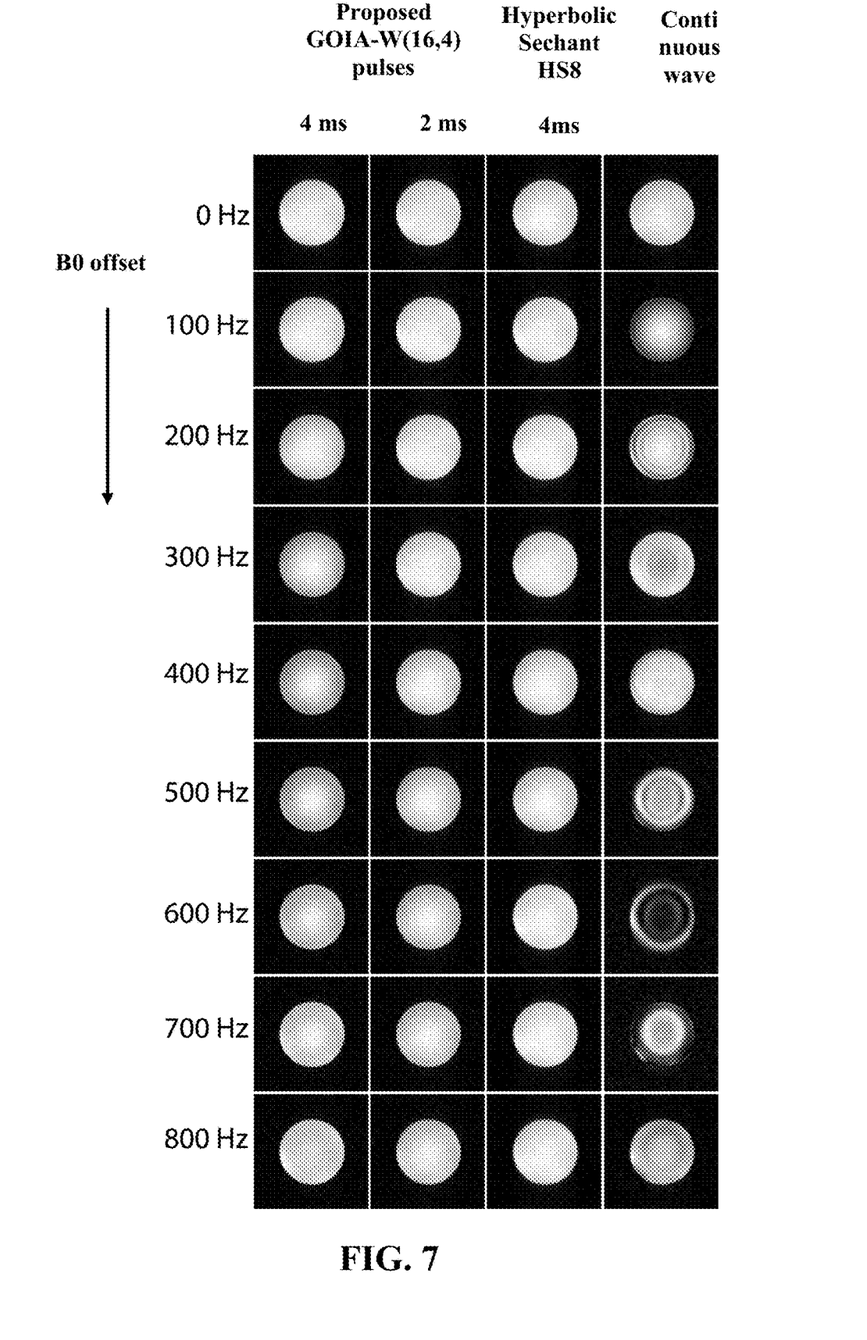
FIG. 7 is an illustration showing an exemplary effect of $B_0$ inhomogeneity on different preparation schemes according to embodiments disclosed herein.

FIG. 7 is an illustration showing the effect of $B_0$ inhomogeneity on different preparation schemes. Despite using $B_0$ and $B_1$ compensation, the continuous wave scheme shows artifacts for offsets of 100 Hz or higher. As shown in FIG. 7, GOIA-W(16,4) pulses may exhibit a much better compensation and image uniformity across a wide range of $B_0$ offsets.

Figure 8:
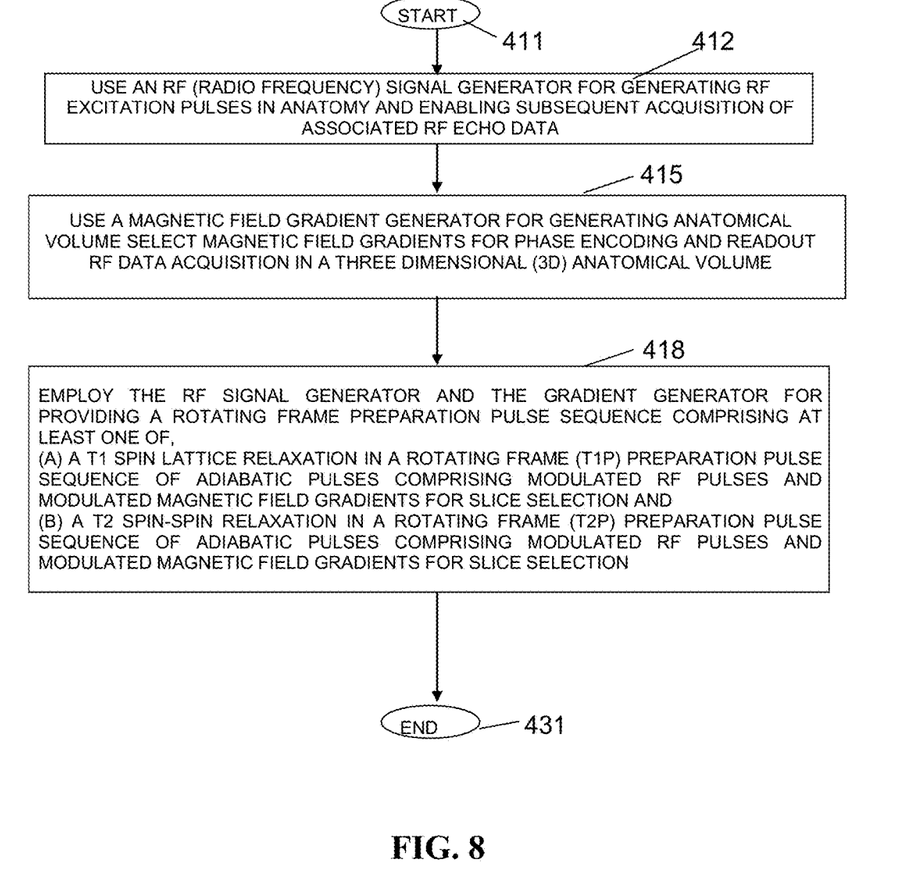
FIG. 8 is a flowchart showing an exemplary process performed by a system for acquiring MR imaging data of a portion of patient anatomy associated with proton spin lattice relaxation time in a rotating frame, according to invention principles.

FIG. 8 is a flowchart showing an exemplary process performed by system 10 for acquiring MR imaging data of a portion of patient anatomy associated with proton spin lattice relaxation time in a rotating frame. In step 412, an RF (Radio Frequency) signal generator (units 18 and 20) generates RF excitation pulses in anatomy and enables subsequent acquisition of associated RF echo data. In step 415, a magnetic field gradient generator (units 12 and 14) generates anatomical volume select magnetic field gradients for phase encoding and readout RF data acquisition in a three dimensional (3D) anatomical volume. In step 418, the RF signal generator and the gradient generator provide a rotating frame preparation pulse sequence comprising at least one of: (a) a T1 spin lattice relaxation in a rotating frame (T1ρ) preparation pulse sequence of adiabatic pulses comprising modulated RF pulses and modulated magnetic field gradients for slice selection; and (b) a T2 spin-spin relaxation in a rotating frame (T2ρ) preparation pulse sequence of adiabatic pulses comprising modulated RF pulses and modulated magnetic field gradients for slice selection. The T1ρ spin lattice relaxation is obtained when proton spin magnetization is locked along the direction of a magnetic field in response to RF pulse amplitude and RF offset modulation. The T2ρ spin-spin relaxation is obtained in response to proton spin magnetization being perpendicular and precessing around the direction of a magnetic field resulting from an RF pulse amplitude and RF offset modulation.

In one embodiment, the RF signal generator and the gradient generator use a readout gradient for RF data acquisition and the rotating frame preparation pulse sequence of adiabatic pulses and readout RF data acquisition enable acquisition of multiple image slices within a single imaging scan. The single imaging scan comprises a programmed acquisition of MR image data without user interaction in controlling an MRI scanner. The readout RF data acquisition comprises at least one of, a spin echo or gradient echo EPI (Echoplanar imaging), TFL (Turbo-FLASH) or TSE (Turbo-spin echo) pulse sequence acquisition. The rotating frame preparation pulse sequence of adiabatic pulses and readout RF data acquisition enable acquisition of the multiple image slices comprising at least one of, (a) 20 slices with EPI based data acquisition within 1.5 minutes, (b) 128 slices with 3D TFL (turbo-FLASH) based data acquisition within 7.21 minutes.

The rotating frame preparation pulse sequence of adiabatic pulses and readout RF data acquisition enable acquisition of the multiple image slices with reduced Specific Absorption Rate enabling accelerated image acquisition of the multiple image slices within a single scan. The modulated RF pulses and modulated magnetic field gradients for slice selection comprise a Gradient Offset Independent Adiabaticity pulse with Wurst modulation (GOIA-W) for both RF and gradient.

According to one embodiment, a modulation function is, $$RF(t) = RF_{max}\left(1 - \left|\sin\left(\frac{\pi}{2}\left(\frac{2t}{T_p} - 1\right)\right)\right|^n\right)$$

$$G(t) = G_{max}\left((1-f) + f\left|\sin\left(\frac{\pi}{2}\left(\frac{2t}{T_p} - 1\right)\right)\right|^m\right)$$

where Tp is the pulse duration (0<t<Tp), RFmax is a maximum RF amplitude, Gmax is a maximum gradient, f [0, 1] is the gradient modulation factor, GOIA-W pulses comprises GOIA-W(n, m), where n and m are the orders for the RF and gradient modulation functions respectively and are chosen to be different (m<n) and the functions comprise at least one of GOIA-W(16,4) and GOIA-W(16,3). The rotating frame preparation pulse sequence of adiabatic pulses acquires multiple different images at corresponding multiple T1ρ or T2ρ preparation times having a range of 0-100 msec. Further, an image data processor generates a composite T1ρ or T2ρ image map from the multiple different images. In one embodiment, the rotating frame preparation pulse sequence of adiabatic pulses enables generation of the composite T1ρ or T2ρ image map from the multiple different images within at least one of, (a) 1.5 minutes with EPI data acquisition and (b) 7.21 minutes with TFL (Turbo-FLASH) based data acquisition. The process of FIG. 8 terminates at step 431.

A processor, as used herein, is a device for executing machine-readable instructions stored on a non-transitory, tangible computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

Terms and Concepts Associated with Some Embodiments

T1rho (or "T-1-rho"), is the spin lattice relaxation time constant in the rotating frame, which determines the recovery of the longitudinal magnetization (along the effective field) in the presence of a "spin-lock" radio-frequency field and is an alternate MRI contrast method to visualize early pathological changes. The rotating frame is defined as the coordinate system that rotates about Z axis at the Larmor frequency of the scanner. In the rotating frame, a magnetization vector rotating at the Larmor frequency in the laboratory frame appears stationary.

GOIA-W(16,4) means: Gradient Offset Independent Adiabaticity with Wurst 16 and 4 modulation, an adiabatic pulse with two modulation functions, one for RF and one for the gradient. For RF uses WURST-16, for gradient it uses WURST-4. GOIA-HS(8,4) based on hyperbolic sechant modulations. Usage of GOIA-W(16,4) pulses to generate T1rho and T2ho contrast is: 1) slice selective, hence a shorter repetition time can be used without saturating spins of an entire subject, 2) require low power deposition to achieve adiabatic rotating frame spin lock and 3) enables reduction in image data acquisition time due to being slice selective and having relatively low SAR.

MLEV-16 and MLEV-4 are Malcom Levitt's sequence with a symmetry of 16 or 4 and are sequences that can be used for heteronuclear decoupling, homonuclear Hartman-Hahn transfer or T1rho.

SAR)—the Specific Absorption Rate is defined as the RF power absorbed per unit of mass of an object, and is measured in watts per kilogram (W/kg).

EPI=Echo planar imaging involves image acquisition whereby a complete image is formed from a single data sample (k-space lines are acquired in one repetition time) of a gradient echo or spin echo sequence.

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted, T2 weighted). Adiabatic IR pulses are used to give more uniform contrast throughout an imaging volume than non-adiabatic RF pulses.

iPAT (integrated Parallel Acquisition Techniques) comprises "parallel imaging". It enables faster scanning through reduced phase encoding and addition of RF coil information. An iPAT factor of 2 enables scanning about twice as fast, iPAT factor of 3 enables scanning about three times as fast and so on.

TI comprises inversion time, the time between an inversion recovery pulse and the next RF excitation pulse. TI determines the image contrast.

$T_1$ comprises the longitudinal (or spin-lattice) relaxation time $T_1$ decay constant.

$T_2$ comprises the transverse (or spin-spin) relaxation time $T_2$ is the decay constant for a proton spin component.

TR comprises repetition time, the time between successive RF excitation pulses.

FA comprises flip angle, i.e., an RF flip angle. For an inversion pulse, FA=180 degrees.

A saturation pulse (or saturation recovery pulse) comprises an RF pulse, typically 90 degrees (or any odd multiple of 90 degrees). Some systems use a spoiler gradient after the RF pulse. In a particular type of partial saturation pulse sequence a preceding pulse leaves the spins in a state of saturation, so that recovery at the time of the next pulse has taken place from an initial condition of no magnetization.

Adiabatic RF pulses=RF amplitude and frequency modulated pulses that are insensitive to the effects of B1-inhomogeneity and frequency offset (conventional RF pulses used in MRI are only amplitude modulated).

RF refocusing pulse=A radio frequency (RF) refocusing (or rephasing) pulse returns spins to the same starting phase that they had after an initial excitation RF pulse (an excitation RF pulse brings the magnetization from the longitudinal direction into the transverse plane). At the time point when the spins have reached the same starting phase, the available signal is maximal.

Spoiler gradient=a magnetic field gradient pulse applied to effectively remove transverse magnetization of a field coil by producing a rapid variation of its phase along the direction of the gradient. For the T2ρprep module it is played after the 90 degrees flip back (also known as tip up) pulse has been played. It destroys remaining transverse magnetization so that after playing the entire T2ρrep module magnetization is again in the longitudinal direction B0 is the main static base MRI magnetic field.

B1 is the RF transmit coil field.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The low power adiabatic MRI T1rho imaging system with increased spatial coverage and short acquisition time uses a T1rho pulse sequence based on low power gradient offset independent adiabatic pulses (Gradient Offset Independent Adiabacity with Wurst 16 and 4 modulation GOIA-W(16,4) pulses, for example) which decreases SAR and allows shorter repetition time TR in multislice acquisition. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both. No claim element herein is to be construed under the provisions of 35 U.S.C. 112, sixth paragraph, unless the element is expressly recited using the phrase "means for."

What is claimed:

1. A system for acquiring MR imaging data of a portion of patient anatomy associated with proton spin lattice relaxation time in a rotating frame, comprising:
   an RF (Radio Frequency) signal generator configured to generate RF excitation pulses in an anatomy and enabling subsequent acquisition of associated RF echo data; and
   a magnetic field gradient generator configured to generate anatomical volume select magnetic field gradients for phase encoding and readout RF data acquisition in a three dimensional (3D) anatomical volume,
   wherein said RF signal generator and said gradient generator provide a rotating frame preparation pulse sequence comprising at least one of:
   (a) a T1 spin lattice relaxation in a rotating frame (T1ρ) preparation pulse sequence of adiabatic pulses comprising modulated RF pulses and modulated magnetic field gradients for slice selection applied simultaneously with the modulated RF pulses; or
   (b) a T2 spin-spin relaxation in a rotating frame (T2ρ) preparation pulse sequence of adiabatic pulses comprising modulated RF pulses and modulated magnetic field gradients for slice selection applied simultaneously with the modulated RF pulses;
   wherein said modulated RF pulses and modulated magnetic field gradients for slice selection comprise a Gradient Offset Independent Adiabaticity pulse with Wurst modulation (GOIA-W).

2. A system according to claim 1, wherein
said RF signal generator and said gradient generator use a readout gradient for RF data acquisition, and said rotating frame preparation pulse sequence of adiabatic pulses and readout RF data acquisition enable acquisition of a plurality of image slices within a single imaging scan.

3. A system according to claim 2, wherein
said single imaging scan comprises a programmed acquisition of MR image data without user interaction in controlling an MRI scanner.

4. A system according to claim 2, wherein
said rotating frame preparation pulse sequence of adiabatic pulses and readout RF data acquisition enable acquisition of said plurality of image slices comprising at least one of: (a) 20 slices with (echo planar imaging) EPI based data acquisition; or (b) 128 slices with 3D TFL (turbo-FLASH) based data acquisition.

5. A system according to claim 4, wherein
said rotating frame preparation pulse sequence of adiabatic pulses and readout RF data acquisition enable acquisition of said plurality of image slices comprising at least one of: (a) 20 slices with EPI based data acquisition within 1.5 minutes; or (b) 128 slices with 3D TFL (turbo-FLASH) based data acquisition within 7.21 minutes.

6. A system according to claim 2, wherein
said rotating frame preparation pulse sequence of adiabatic pulses and readout RF data acquisition enable acquisition of said plurality of image slices with a Specific Absorption Rate enabling accelerated image acquisition of said plurality of image slices within a single scan.

7. A system according to claim 1, wherein
said T1ρ spin lattice relaxation is obtained when proton spin magnetization is locked along the direction of an effective magnetic field in response to RF pulse amplitude and RF offset modulation.

8. A system according to claim 1, wherein
said T2ρ spin-spin relaxation is obtained in response to proton spin magnetization being perpendicular and precessing around the direction of an effective magnetic field resulting from an RF pulse amplitude and RF offset modulation.

9. A system according to claim 1, wherein a modulation function is;

$$RF(t) = RF_{max}\left(1 - \left|\sin\left(\frac{\pi}{2}\left(\frac{2t}{T_p} - 1\right)\right)\right|^n\right)$$

$$G(t) = G_{max}\left((1-f) + f\left|\sin\left(\frac{\pi}{2}\left(\frac{2t}{T_p} - 1\right)\right)\right|^m\right)$$

where Tp is the pulse duration (0<t<Tp), RFmax is a maximum RF amplitude, Gmax is a maximum gradient, f [0, 1] is the gradient modulation factor, GOIA-W pulses comprises GOIAW(n, m), where n and m are the orders for the RF and gradient modulation functions respectively and are chosen to be different (m<n) and the functions comprise at least one of GOIA-W(16,4) or GOIA-W(16,3).

10. A system according to claim 1, wherein
said rotating frame preparation pulse sequence of adiabatic pulses acquires a plurality of different images at a corresponding plurality of T1ρ or T2ρ preparation times having a range of 0-100 msec, and
further comprising an image data processor configured to generate a composite T1ρ or T2ρ image map from said plurality of different images.

11. A system according to claim 10, wherein
said rotating frame preparation pulse sequence of adiabatic pulses enables generation of said composite T1ρ or T2ρ image map from said plurality of different images within at least one of, (a) 1.5 minutes with EPI data acquisition or (b) 7.21 minutes with TFL (Turbo-FLASH) based data acquisition.

12. A system according to claim 2, wherein
said readout RF data acquisition comprises at least one of: a spin echo or gradient echo EPI (Echoplanar imaging); TFL (Turbo-FLASH); or TSE (Turbo-spin echo) pulse sequence acquisition.

13. A method for acquiring MR imaging data of a portion of patient anatomy associated with proton spin lattice relaxation time in a rotating frame, comprising:
generating, via an RF (Radio Frequency) signal generator, RF excitation pulses in an anatomy;
enabling, via said RF (Radio Frequency) signal generator, subsequent acquisition of associated RF echo data; and
generating, via a magnetic field gradient generator, anatomical volume select magnetic field gradients for phase encoding and readout RF data acquisition in a three dimensional (3D) anatomical volume, said RF signal generator and said gradient generator providing a rotating frame preparation pulse sequence comprising at least one of:
(a) a T1 spin lattice relaxation in a rotating frame (T1ρ) preparation pulse sequence of adiabatic pulses comprising modulated RF pulses and modulated magnetic field gradients for slice selection applied simultaneously with the modulated RF pulses; or
(b) a T2 spin-spin relaxation in a rotating frame (T2ρ) preparation pulse sequence of adiabatic pulses comprising modulated RF pulses and modulated magnetic field gradients for slice selection applied simultaneously with the modulated RF pulses;
wherein said modulated RF pulses and modulated magnetic field gradients for slice selection comprise a Gradient Offset Independent Adiabaticity pulse with Wurst modulation (GOIA-W).

14. A method according to claim 13, further comprising using a readout gradient for RF data acquisition, and
wherein said rotating frame preparation pulse sequence of adiabatic pulses and readout RF data acquisition enable acquisition of a plurality of image slices within a single imaging scan.

15. A method according to claim 14, wherein
said single imaging scan comprises a programmed acquisition of MR image data without user interaction in controlling an MRI scanner.

16. A method according to claim 14, wherein
said rotating frame preparation pulse sequence of adiabatic pulses and readout RF data acquisition enable acquisition of said plurality of image slices comprising at least one of: (a) 20 slices with (echo planar imaging) EPI based data acquisition; or (b) 128 slices with 3D TFL (turbo-FLASH) based data acquisition.

17. A method according to claim 16, wherein
said rotating frame preparation pulse sequence of adiabatic pulses and readout RF data acquisition enable acquisition of said plurality of image slices comprising at least one of: (a) 20 slices with EPI based data acquisition within 1.5 minutes; or (b) 128 slices with 3D TFL (turbo-FLASH) based data acquisition within 7.21 minutes.

18. A method according to claim 14, wherein
said rotating frame preparation pulse sequence of adiabatic pulses and readout RF data acquisition enable acquisition of said plurality of image slices with Specific Absorption Rate enabling accelerated image acquisition of said plurality of image slices within a single scan.

19. A method according to claim 13, wherein
said T1ρ spin lattice relaxation is obtained when proton spin magnetization is locked along the direction of a magnetic field in response to RF pulse amplitude and RF offset modulation.

20. A method according to claim 13, wherein
said T2ρ spin-spin relaxation is obtained in response to proton spin magnetization being perpendicular and precessing around the direction of a magnetic field resulting from an RF pulse amplitude and RF offset modulation.

21. A method according to claim 13, wherein
said rotating frame preparation pulse sequence of adiabatic pulses acquires a plurality of different images at a corresponding plurality of T1ρ or T2ρ preparation times having a range of 0-100 msec, and
further comprising generating, via an image data processor, a composite T1ρ or T2ρ image map from said plurality of different images.

22. A method according to claim 14, wherein
said readout RF data acquisition comprises at least one of: a spin echo or gradient echo EPI (Echoplanar imaging); TFL (Turbo-FLASH) or TSE (Turbo-spin echo) pulse sequence acquisition.

23. A non-transitory, tangible computer-readable medium having instructions stored thereon for causing a processor to execute a method for acquiring MR imaging data of a portion of patient anatomy associated with proton spin lattice relaxation time in a rotating frame, comprising:
generating RF excitation pulses in an anatomy;
enabling subsequent acquisition of associated RF echo data;
generating anatomical volume select magnetic field gradients for phase encoding and readout RF data acquisition in a three dimensional (3D) anatomical volume; and
providing a rotating frame preparation pulse sequence comprising at least one of:
(a) a T1 spin lattice relaxation in a rotating frame (T1ρ) preparation pulse sequence of adiabatic pulses comprising modulated RF pulses and modulated magnetic field gradients for slice selection applied simultaneously with the modulated RF pulses; or
(b) a T2 spin-spin relaxation in a rotating frame (T2ρ) preparation pulse sequence of adiabatic pulses comprising modulated RF pulses and modulated magnetic field gradients for slice selection applied simultaneously with the modulated RF pulses;
wherein said modulated RF pulses and modulated magnetic field gradients for slice selection comprise a Gradient Offset Independent Adiabaticity pulse with Wurst modulation (GOIA-W).

24. A system for acquiring MR imaging data of a portion of patient anatomy associated with proton spin lattice relaxation time in a rotating frame, comprising:
an RF (Radio Frequency) signal generator configured to generate RF excitation pulses in an anatomy and enabling subsequent acquisition of associated RF echo data; and a magnetic field gradient generator configured to generate anatomical volume select magnetic field gradients for phase encoding and readout RF data acquisition in a three dimensional (3D) anatomical volume simultaneously with the generation of RF excitation by the RF signal generator, wherein said RF signal generator and said gradient generator provide a rotating frame preparation pulse sequence comprising at least one of:

(a) a T1 spin lattice relaxation in a rotating frame (T1ρ) preparation pulse sequence of adiabatic pulses comprising modulated RF pulses and modulated magnetic field gradients for slice selection; or (b) a T2 spin-spin relaxation in a rotating frame (T2ρ) preparation pulse sequence of adiabatic pulses comprising modulated RF pulses and modulated magnetic field gradients for slice selection;

wherein said rotating frame preparation pulse sequence of adiabatic pulses acquires a plurality of different images at a corresponding plurality of T1ρ or T2ρ preparation times having a range of 0-100 msec;

the system further comprising an image data processor configured to generate a composite T1ρ or T2ρ image map from said plurality of different images.

25. A method for acquiring MR imaging data of a portion of patient anatomy associated with proton spin lattice relaxation time in a rotating frame, comprising:

generating, via an RF (Radio Frequency) signal generator, RF excitation pulses in an anatomy;

enabling, via said RF (Radio Frequency) signal generator, subsequent acquisition of associated RF echo data; and simultaneously with the generation of RF excitation pulses generating, via a magnetic field gradient generator, anatomical volume select magnetic field gradients for phase encoding and readout RF data acquisition in a three dimensional (3D) anatomical volume, said RF signal generator and said gradient generator providing a rotating frame preparation pulse sequence comprising at least one of:

(a) a T1 spin lattice relaxation in a rotating frame (T1ρ) preparation pulse sequence of adiabatic pulses comprising modulated RF pulses and modulated magnetic field gradients for slice selection; or (b) a T2 spin-spin relaxation in a rotating frame (T2ρ) preparation pulse sequence of adiabatic pulses comprising modulated RF pulses and modulated magnetic field gradients for slice selection;

wherein said rotating frame preparation pulse sequence of adiabatic pulses acquires a plurality of different images at a corresponding plurality of T1ρ or T2ρ preparation times having a range of 0-100 msec;

the method further comprising generating, via an image data processor, a composite T1ρ or T2ρ image map from said plurality of different images.

26. A non-transitory, tangible computer-readable medium having instructions stored thereon for causing a processor to execute a method for acquiring MR imaging data of a portion of patient anatomy associated with proton spin lattice relaxation time in a rotating frame, comprising:

generating RF excitation pulses in an anatomy;

enabling subsequent acquisition of associated RF echo data;

generating anatomical volume select magnetic field gradients for phase encoding and readout RF data acquisition in a three dimensional (3D) anatomical volume; and simultaneously with the generation of RF excitation pulses, providing a rotating frame preparation pulse sequence comprising at least one of:

(a) a T1 spin lattice relaxation in a rotating frame (T1ρ) preparation pulse sequence of adiabatic pulses comprising modulated RF pulses and modulated magnetic field gradients for slice selection; or (b) a T2 spin-spin relaxation in a rotating frame (T2ρ) preparation pulse sequence of adiabatic pulses comprising modulated RF pulses and modulated magnetic field gradients for slice selection;

wherein said rotating frame preparation pulse sequence of adiabatic pulses acquires a plurality of different images at a corresponding plurality of T1ρ or T2ρ preparation times having a range of 0-100 msec;

the processor further executing a step of generating, via an image data processor, a composite T1ρ or T2ρ image map from said plurality of different images.

* * * * *